US010610174B1

(12) United States Patent
O'Brien et al.

(10) Patent No.: US 10,610,174 B1
(45) Date of Patent: Apr. 7, 2020

(54) WHEEL ALIGNMENT GUIDE FOR MEDICAL EQUIPMENT AND METHOD OF USE

(71) Applicant: The Parking Space, LLC, Tampa, FL (US)

(72) Inventors: Graig Thomas O'Brien, Tampa, FL (US); Jon Kimball, Tampa, FL (US)

(73) Assignee: The Parking Space, LLC, Tampa, FL (US)

( * ) Notice: Subject to any disclaimer, the term of this patent is extended or adjusted under 35 U.S.C. 154(b) by 0 days.

(21) Appl. No.: 16/577,289

(22) Filed: Sep. 20, 2019

Related U.S. Application Data

(63) Continuation-in-part of application No. 16/021,828, filed on Jun. 28, 2018, which is a continuation of application No. 15/853,296, filed on Dec. 22, 2017, now Pat. No. 10,034,642.

(51) Int. Cl.
*A61B 6/04* (2006.01)
*A61B 6/00* (2006.01)
*G01B 11/275* (2006.01)

(52) U.S. Cl.
CPC .......... *A61B 6/4405* (2013.01); *A61B 6/0407* (2013.01); *A61B 6/587* (2013.01); *G01B 11/275* (2013.01); *G01B 2210/303* (2013.01)

(58) Field of Classification Search
CPC .............................. A61N 5/10; A61N 2005/10
See application file for complete search history.

(56) References Cited

U.S. PATENT DOCUMENTS

| 5,339,350 | A | * | 8/1994 | Thelosen | A61B 6/4405 378/194 |
|---|---|---|---|---|---|
| 5,873,144 | A | * | 2/1999 | Tupper | B60B 7/02 16/18 CG |
| 6,678,917 | B1 | * | 1/2004 | Winters | B60B 7/00 16/18 CG |
| 10,034,642 | B1 | * | 7/2018 | O'Brien | G01B 21/26 |

* cited by examiner

*Primary Examiner* — Thomas R Artman
(74) *Attorney, Agent, or Firm* — Smith & Hopen, P.A.; Paul Murty

(57) ABSTRACT

A wheel alignment guide that provides a visual indication of the desired placement of an apparatus. The wheel alignment guide includes one or more body members defining an opening to surround a portion of the apparatus, such as a wheel. The wheel of the apparatus is disposed within the opening of the wheel alignment guide after a desired position of the apparatus is selected, and the wheel may be pivoted via concave edges of the one or more body members. If the apparatus is moved during operation, the apparatus may be repositioned due to the placement of the wheel alignment guide. Accordingly, the wheel alignment guide eliminates the need for inefficient markers and potentially-dangerous adhesives, particularly in an operating room.

20 Claims, 7 Drawing Sheets

WHEEL ALIGNMENT GUIDE FOR MEDICAL EQUIPMENT AND METHOD OF USE

CROSS-REFERENCE TO RELATED APPLICATIONS

This nonprovisional application is a continuation-in-part of and claims priority to nonprovisional application Ser. No. 16/021,828, entitled "WHEEL ALIGNMENT GUIDE FOR MEDICAL EQUIPMENT AND METHOD OF USE," filed on Jun. 28, 2018, which is a continuation of and claims priority to nonprovisional application Ser. No. 15/853,296, entitled "WHEEL ALIGNMENT GUIDE FOR MEDICAL EQUIPMENT AND METHOD OF USE," filed on Dec. 22, 2017, and issued as U.S. Pat. No. 10,034,642 on Jul. 31, 2018, each of which is by the same inventors and is incorporated herein by reference.

BACKGROUND OF THE INVENTION

1. Field of the Invention

This invention relates, generally, to a wheel alignment guide and a method of use. More specifically, it relates to a wheel alignment guide for use with medical equipment in an operation room, such that medical professionals can correctly align medical equipment with respect to the patient's body.

2. Brief Description of the Prior Art

It is important to correctly position medical equipment according to the needs of a medical procedure. For example, a fluoroscopy machine must align with a patient at a particular angle to scan a target area. To correctly align with patients having different body types and characteristics, equipment often must be repositioned. In addition, during a medical procedure, a medical professional may need to move the equipment away from the patient, thereby allowing unobstructed access to the patient. The equipment must then be repositioned to be used on the patient. In the case of a fluoroscopy machine, the angle must match the initial angle; otherwise, the machine will provide an incorrect scan of the target area, which can cause complications to the procedure.

Currently, medical professionals use a variety of indicators to guide machine realignment. One method of providing a visual indication is to mark the floor with a marker, highlighter, or other writing implement. By marking the floor in such a way, a medical professional can generally guide a machine to its initial position. However, marking the floor does not represent an ideal solution. For example, there is a possibility that the mark will be erased during a procedure. In addition, if the machine must be repositioned to accommodate multiple patients, different marks will be placed on the floor. The marks are not only aesthetically unpleasant, but also increase the likelihood that an incorrect mark will be chosen.

Another method of providing a visual indication is to use an adhesive to mark the correct spot. However, adhesives also suffer from several drawbacks, making their use a less-than-ideal solution. For example, adhesives may leave remnant residue on the floor that can cause misalignment of machinery, as well as present a danger to machinery and personnel if the floor is sticky. In addition, the use of adhesives may cause bacterial or fungal growth in an otherwise sterile environment. Organism growth can cause medical complications for the patient and other personnel within the room, particularly during a surgical procedure. As such, adhesives used within a sterile environment can put the patient and others at risk of infection and other diseases and disorders.

Accordingly, what is needed is a device and method of aligning medical equipment, allowing the equipment to be moved and repositioned during a medical procedure. However, in view of the art considered as a whole at the time the present invention was made, it was not obvious to those of ordinary skill in the field of this invention how the shortcomings of the prior art could be overcome.

BRIEF SUMMARY OF THE INVENTION

The long-standing but heretofore unfulfilled need for a wheel alignment guide for use with medical equipment in an operation room is now met by a new, useful, and nonobvious invention.

The novel structure includes a body member having a distal end opposite a proximal end, with a plurality of edges defining a perimeter of the body member. The body member also includes a top side opposite a bottom side, with the top and bottom sides being separated by a plurality of edges, one or more of which may taper from the bottom side to the top side, such that the bottom side has a greater surface area than the top side. The bottom side is configured to rest on a ground surface. In an embodiment, the bottom side securely couples to the ground surface via an electrostatic connection. Alternatively, the bottom side includes a magnetic or electric charge, forming a connection with a complementary charge on the ground surface. The body member may be made of a flexible material, such as static cling vinyl.

The body member includes a pair of opposing concave edges disposed at the proximal end, with each concave edge extending toward the distal end. A portion of the perimeter of the body member that is defined by the proximal end is sized and shaped to receive a wheel of medical device. Each concave edge is adapted to allow the wheel to pivot between lateral and longitudinal orientations with respect to the body member, with the lateral orientation being parallel to a lateral axis of the guide, and the longitudinal orientation being parallel to a longitudinal axis of the guide.

The wheel alignment guide may include a first body member spaced apart from a second body member by a gap, with the first and second body members defining an opening therebetween. The second body member is similar in shape and orientation to the first body member, such that the second body member includes a distal end opposite a proximal end with a pair of opposing concave edges disposed at the proximal end, with each concave edge extending toward the distal end. The portion of the perimeter of the first body member defined by the proximal end and a portion of a perimeter of the second body member defined by the proximal end together define an opening that is configured to receive the wheel of the medical device. In an embodiment, the opening is cross-shaped, including a first portion that is perpendicular to a second portion. The first and second portions intersect at their respective midpoints, forming a cross-shape. The first and second portions are connected through the plurality of concave edges of the one or more body members.

The body includes an opening extending therethrough from the top side to the bottom side. The opening is cross-shaped, including a first portion that is perpendicular to a second portion. The first and second portions intersect at their respective midpoints, forming a cross-shape. The first and second portions are connected through a plurality of concave interior edges on the body.

In an embodiment, the perimeter of either the first or second body member is defined by a distal longitudinal edge spanning along a longitudinal axis of the body member; a pair of opposing lateral edges extending perpendicularly away from opposing ends of the distal longitudinal edge along a lateral axis of the body member a pair of proximal longitudinal edges partially extending perpendicularly away from one of the pair of lateral edges toward a central, bisectional axis of the body member; a pair of L-shaped edges coupled to each of the pair of proximal longitudinal edges extending toward the central axis of the body member; and a pair of concave edges coupled to each of the pair of L-shaped edges, with each concave edge extending toward the central axis of the body member. The perimeter of the first body member and a perimeter of the second body member may together define the opening that is configured to receive the wheel of the medical device.

An embodiment of the present invention includes a secondary orientation guide including a perimeter that is sized and shaped to be removably received within the opening of the wheel alignment guide. The secondary orientation guide includes at least one detachable alignment indicia configured to indicate an orientation of the medical device. Each alignment indicia includes a bottom surface of a flexible static cling vinyl material that is adapted to securely couple to a surface of the medical device via an electrostatic connection.

An object of the invention is to provide visual identification of the correct placement of a medical device. The invention utilizes a novel wheel alignment guide that eliminates the need to use inefficient markers or potentially-harmful adhesives. Using the wheel alignment guide allows for the repositioning of the medical device, improving the efficiency and safety of a medical procedure.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes a wheel alignment guide and methods of use. The wheel alignment guide is configured to rest on a ground surface and provide a stationary visual indicator for the positioning of a medical device. In addition, the wheel alignment guide is adapted to aid in the repositioning of the medical device such that a position can be replicated after the medical device has been moved. The wheel alignment guide allows a medical professional to move a medical device away from a patient, and later accurately replicate the original position of the medical device, eliminating the need for inefficient markers and potentially-dangerous adhesives.

Figure 1A:
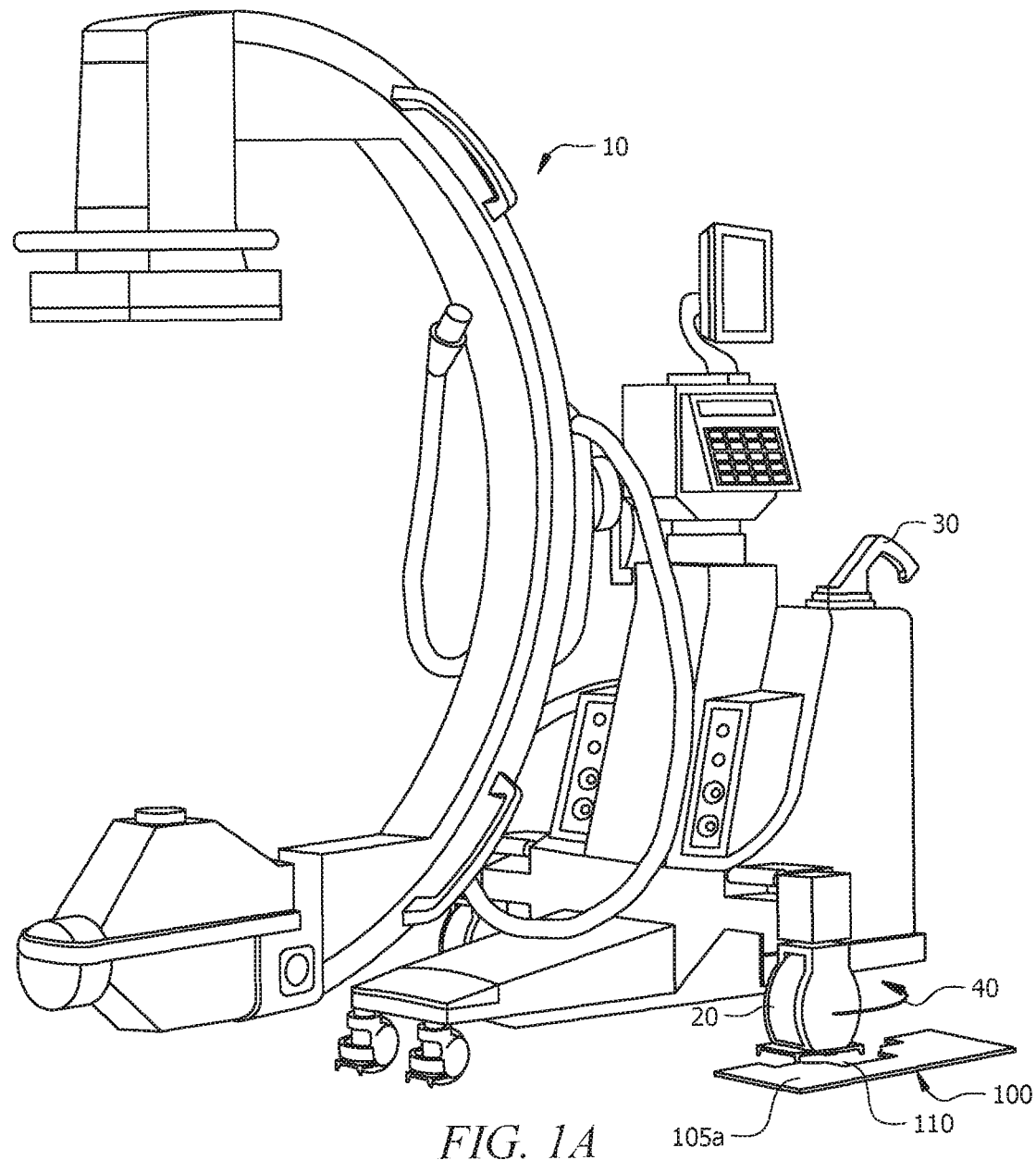
FIG. 1A is a perspective view of a wheel alignment guide including a singular body member used in combination with a medical device having a wheel, in accordance with an embodiment of the present invention.

As shown in FIG. 1A, an embodiment of wheel alignment guide 100, adapted to be used in combination with medical device 10, is shown in detail. Medical device 10 includes at least one wheel 20, and is configured to translate along a ground surface via wheel 20. Wheel 20 is actuated by handle 30, with handle 30 configured to rotatably translate wheel 20 with respect to the ground surface. The rotational translation of wheel 20 is generally denoted as reference numeral 40. Medical device 10 is depicted as a fluoroscopy machine; however, it is appreciated that other movable devices may be used in combination with wheel alignment guide 100.

As shown in the embodiment of FIG. 1A, wheel alignment guide 100 includes body member 105a, which includes a plurality of surfaces or edges that define opening 110. Body member 105a may be referred to as a first body member 105a, and the plurality of surfaces or edges defining opening 110 will be discussed in greater detail below. Opening 110 is adapted to receive wheel 20 of medical device 10, as shown in FIG. 1A. As such, wheel alignment guide 100 is configured to at least partially surround wheel 20 of medical device 10. Wheel alignment guide 100 thereby is adapted to serve as a visual indicator for a position of medical device 10. For example, if medical device 10 is axially translated along the ground surface, medical device 10 can be repositioned in its original position by disposing wheel 20 at least partially within opening 110 of wheel alignment guide 100.

Figure 1B:
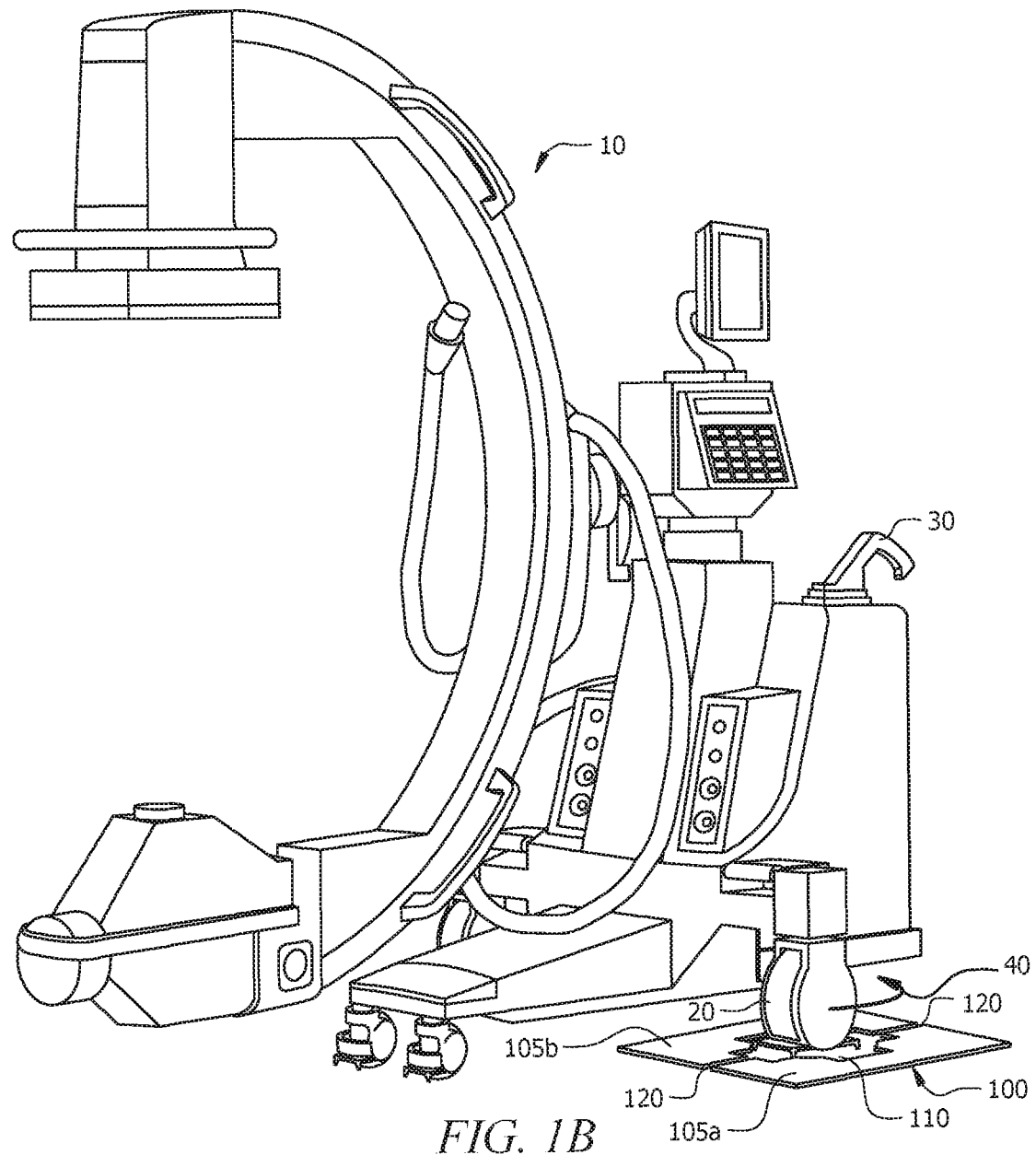
FIG. 1B is a perspective view of a wheel alignment guide including adjacent body members used in combination with a medical device having a wheel, in accordance with an embodiment of the present invention.

As shown in FIG. 1B, an embodiment of wheel alignment guide 100 includes first body member 105a disposed adjacent to second body member 105b, with one or more gaps 120 disposed between adjacent longitudinal edges of first body member 105a and second body member 105b. First body member 105a and second body member 105b together define opening 110 therebetween, and together surround wheel 20, within opening 110, as shown in FIG. 1B. Similar to the embodiment of wheel alignment guide 100 depicted in FIG. 1A, the embodiment of wheel alignment guide 100 depicting in FIG. 1A is sized and shaped such that opening 110 is adapted to receive wheel 20 of medical device therein, such that wheel 20 can rotate between a lateral and a longitudinal orientation within opening 110 without interference from wheel alignment guide 100. The rotation of wheel 20 will be discussed in greater detail below in relation to the plurality of surfaces or edges of each of first and second body members 105a, 105b that define opening 110.

Figure 2:
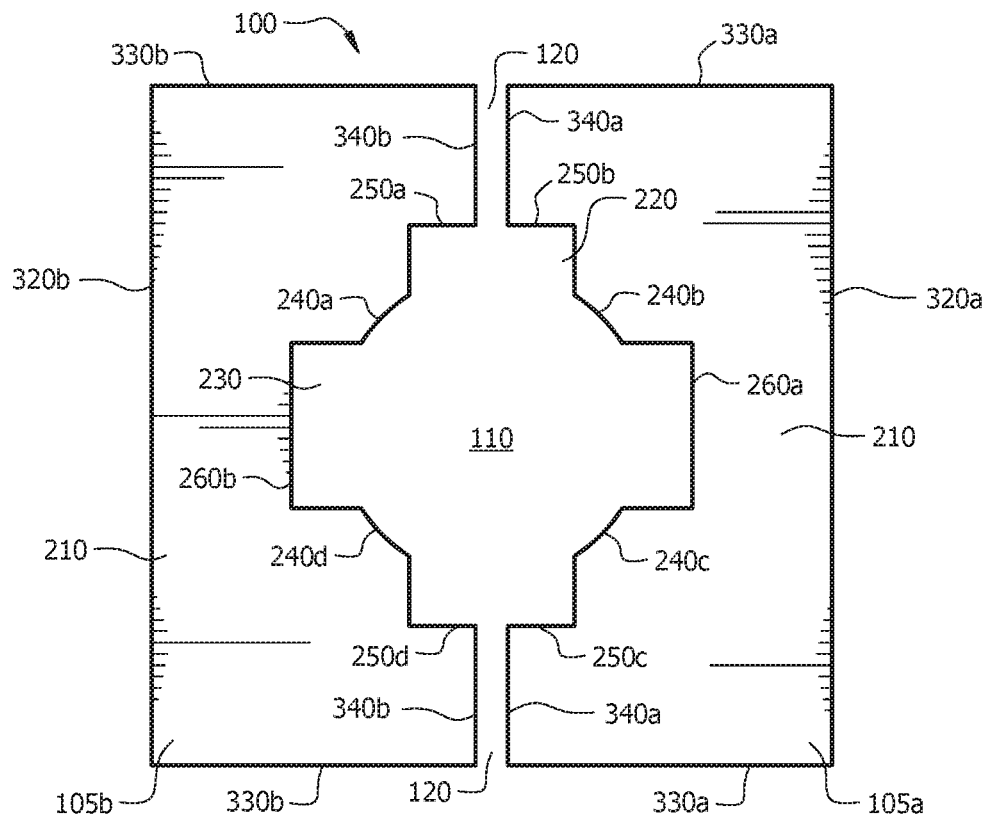
FIG. 2 is a bottom plan view of the wheel alignment guide of FIG. 1B.

Wheel alignment guide 100 is shown in greater detail in FIG. 2, which represents a bottom plan view of first body member 105a disposed adjacent to second body member 105b. Each body member includes bottom side 210 (for example, bottom side 210a of first body member 105a, and bottom side 210b of second body member 105b-collectively referred to as bottom side 210) that is configured to rest on a ground surface when wheel alignment guide 100 is in use. It is important that wheel alignment guide 100 remains substantially stationary on the ground surface, since wheel alignment guide 100 is used to accurately align medical device 10. If wheel alignment guide 100 translates along the ground surface, it will be difficult to correctly align medical device 10. Accordingly, in an embodiment, each bottom side 210 includes a charge that is adapted to form a connection with a complementary charge of the ground surface. For example, the charge may be a magnetic charge that is adapted to magnetically couple with a corresponding magnet disposed on or within the ground surface. Alternatively, the charge may be an electric charge that is adapted to electrically couple with a corresponding charge of the ground surface. In an alternative embodiment, each bottom side 210 is made of a static cling vinyl material that is adapted to securely couple to the ground surface. The static cling vinyl material allows each bottom side 210 to adhere to the ground surface via electrostatic forces, rather than adhesives. It is appreciated that alternative materials may be used to form each bottom side 210, so long as the materials are adapted to form a connection with the ground surface. Regardless of the method, each bottom side 210 rests on and secures to the ground surface to maintain a chosen position of wheel alignment guide 100.

The plurality of surfaces or edges of each body member 105 are also shown in detail in FIG. 2, with the surfaces defining opening 110. As shown in FIG. 2, first body member 105a includes distal longitudinal edge 320a which spans along a longitudinal axis of first body member 105a. First body member 105a also includes a pair of opposing lateral edges 330a that extend perpendicularly from distal longitudinal edge 320a along a lateral axis of first body member 105a. A pair of opposing proximal longitudinal edges 340a extend perpendicularly from each of the opposing lateral edges 330a, with proximal longitudinal edges 340a being parallel to distal longitudinal edge 320a. Each of the proximal longitudinal edges 340a extend away from respective lateral edges 330a toward a central axis that bisects first body member 105a in the lateral direction; however, as shown in FIG. 2, each of the proximal longitudinal edges 340a includes a terminal end that is disposed between respective lateral edges 330a and the central, bisectional axis of first body member 105a. The terminal end of each of the proximal longitudinal edges 340a forms a L-shaped edge that functions as a cutout of first body member 105a; the pair of L-shaped edges of first body member 105a are denoted by reference numerals 250b and 250c. Each L-shaped edge 250b, 250c terminates to form respective concave edges 240b, 240c, respectively. Concave edges 240b and 240c function as curved edges that connect respective L-shaped edges 250b, 250c with the surfaces of first body member 105a that are disposed adjacent to the central, bisectional axis of first body member 105a. As such, concave edges 240b, 240c each terminate to form a lateral edge that connects to central longitudinal edge 260a that is parallel to distal longitudinal edge 320a and proximal longitudinal edges 340a. Central longitudinal edge 260a is disposed between distal longitudinal edge 320a and proximal longitudinal edges 340a along the lateral axis of first body member 105a.

While the description above focuses on first body member 105a, as shown in FIG. 2, second body member 105b includes similar edges and surfaces to form a shape that is similar to that of first body member 105a. As such, second body member 105b includes distal longitudinal edge 320b and proximal longitudinal edges 340b joined by lateral edges 330b that are perpendicular to each of distal longitudinal edge 320b and proximal longitudinal edges 340b. In addition, second body member 105b includes L-shaped edges 250a, 250d that terminate to form concave edges 240a, 240d, respectively. Concave edges 250a, 250d terminate in lateral edges that form central longitudinal edge 260b that is parallel to and disposed between distal longitudinal edge 320b and proximal longitudinal edges 240b.

As shown in FIG. 2, first and second body members 105a, 105b together define opening 110 disposed therebetween, with gaps 120 existing between the adjacent first and second body members 105a, 105b. Opening 110 is shown as being cross-shaped, including first portion 220 and second portion 230. First portion 220 and second portion 230 intersect at their respective midpoints to from the cross-shape. As shown in FIG. 2, first portion 220 of opening 110 spans between L-shaped edges 250a, 250b and L-shaped edges 250d, 250c, respectively. Accordingly, a longitudinal distance between respective L-shaped edges of the same body member and a lateral distance between adjacent L-shaped edges of opposite body members are sized to receive wheel 20 of medical device 10. In addition, second portion 230 of opening 110 spans between central longitudinal edge 260a of first body member 105a and central longitudinal edge 260b of second body member 105b. Similar to first portion 220 discussed above, the lateral distance between central longitudinal edges 260a, 260b, and the longitudinal length of each longitudinal edge 260a, 260b are sized to receive wheel 20 of medical device 10. Accordingly, first and second portions 220, 230 are each sized to receive wheel 20 of medical device 10, depending on an orientation of wheel 20.

In addition, the shape and orientation of each of first body member 105a and second body member 105b is such that wheel 20 can rotate within opening 110. The plurality of concave edges 240a-d are sized, shaped, and positioned to allow wheel 20 to pivot between first portion 220 and second portion 230, providing a path via which wheel 20 can rotatably translate between first and second portions 220, 230, without obstacle or interruption. Such an unimpeded path is an important feature of wheel alignment guide 100, because an obstacle could make medical device 10 unstable and prone to tipping. Specifically, if wheel 20 is disposed within first portion 220 of opening 110 and oriented along the longitudinal axis of body member 105, wheel is capable of rotationally translating along concave edge 240b of first body member 105a and concave edge 240d of second body member 105b. After the unimpeded rotational translation, wheel 20 is disposed within second portion 230 of opening 110 and oriented along the longitudinal axis of body member 105. Similarly, to rotationally translate from second portion 230 to first portion 220, wheel 20 may translate in a reverse direction along concave edges 240b, 240d.

It is appreciated that wheel 20 may alternatively rotate along concave edge 240c of first body member 105a and concave edge 240a of second body member 105b to be disposed within first portion 220. As such, it is appreciated that in certain embodiments, only diagonally-opposing concave edges may be formed by adjacent body members, depending on a rotational translation of wheel. For example, first body member 105a may include only concave edge 240b and second body member 105b may include only concave edge 240d, such that wheel 20 rotationally translates along concave edges 240b, 240d between first portion 220 and second portion 230 of opening 110. Moreover, it is appreciated that, as shown in FIG. 1A, only one body member may partially surround wheel 20 to provide an alignment guide, and that wheel 20 rotationally translated between longitudinal and lateral orientations along one or more of concave edges 240b, 240c.

Figure 3:
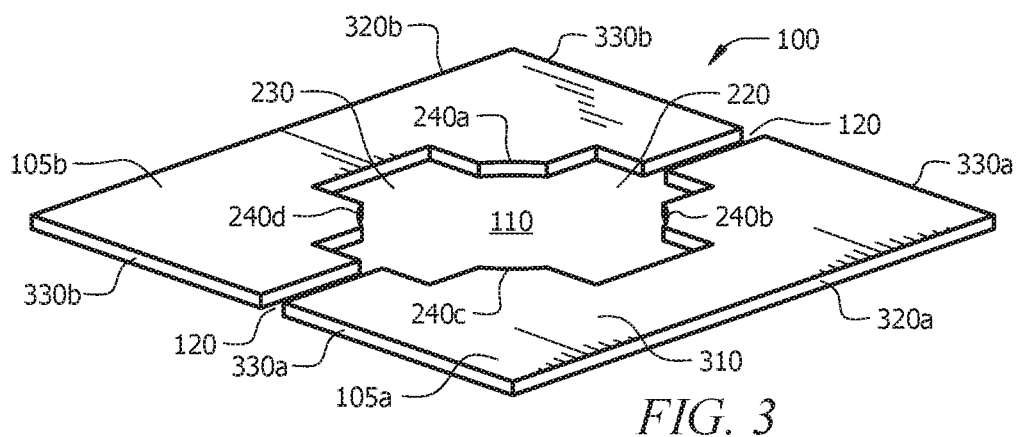
FIG. 3 is a perspective view of the wheel alignment guide of FIG. 1B.

Turning now to FIG. 3, wheel alignment guide 100 is shown in a top-side perspective view. Each body member includes top side 310 (for example, top side 310a of first body member 105a, and top side 310b of second body member 105b-collectively referred to as top side 310), which is opposite bottom side 210 (shown in FIG. 2 and described above). FIG. 3 depicts top side 310 and bottom side 210 of each body member having substantially identical surface areas, with the edges discussed in detail above (for example, collective distal longitudinal edges 320, lateral edges 330, proximal longitudinal edges 340, L-shaped edges 250, concave edges 240, and central longitudinal edges 260). Medical device 10 can translate along the ground surface and overcome one or more of these edges, as well as top side 310, to dispose wheel 20 within opening 110, similar to a vehicle overcoming a speed bump. However, it is appreciated that top side 310 may have a smaller surface area than bottom side 210, with one or more tapers being formed between top side 310 and bottom side 210 along one or more of the edges discussed in detail above. The use of one or more tapered edges may facilitate the translation of medical device 10, since wheel 20 would have a shortened distance to overcome the tapered edge.

Figure 4:
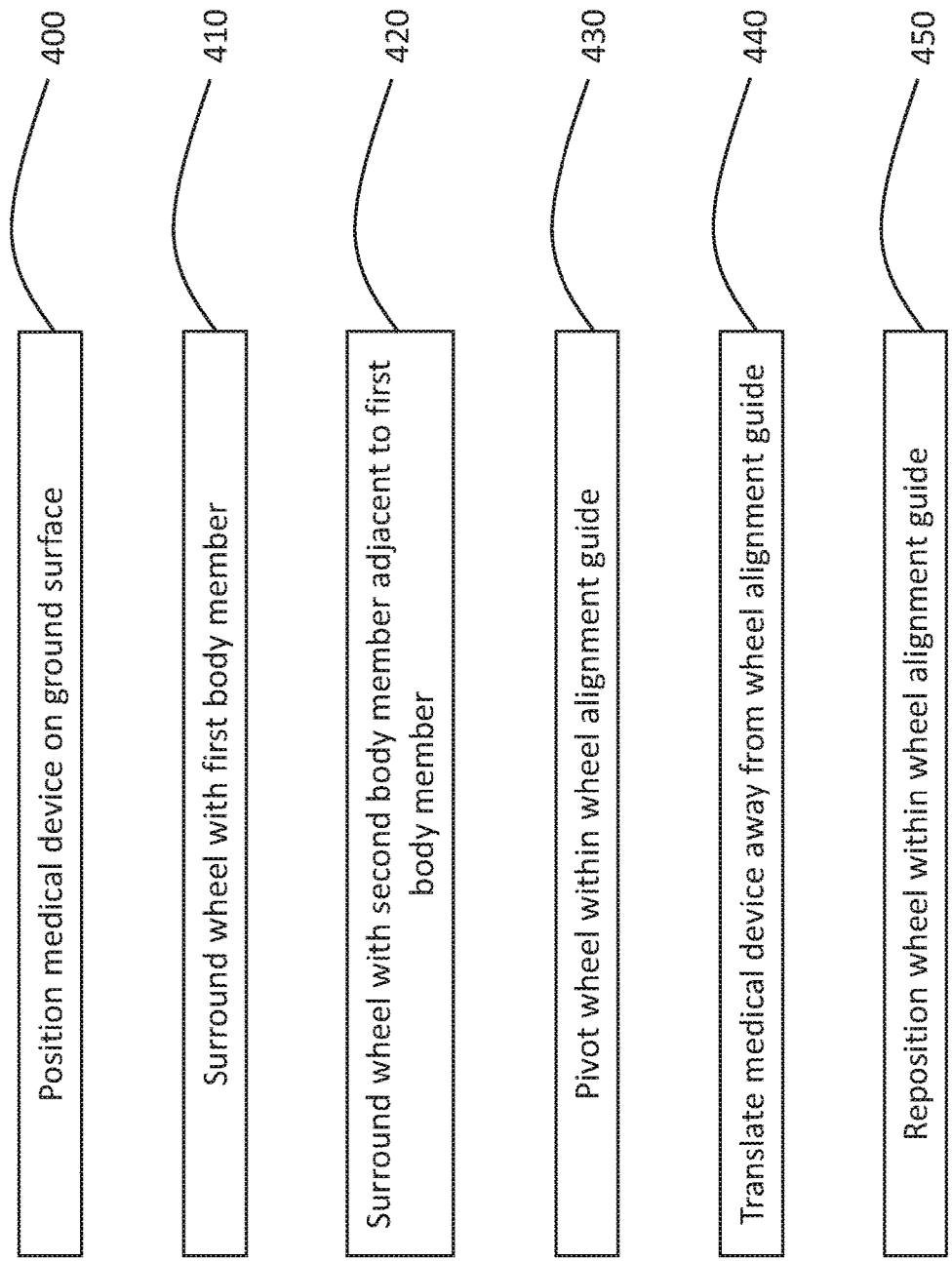
FIG. 4 is a flow chart diagram describing a method of aligning a wheel of a medical device, in accordance with the present invention.

Referring now to FIG. 4, in conjunction with FIGS. 1-3, an exemplary process-flow diagram is provided, depicting a method of aligning a wheel of a medical device. The steps delineated in the exemplary process-flow diagram of FIG. 4 are merely exemplary of an order of aligning a wheel of a medical device. The steps may be carried out in another order, with or without additional steps included therein.

The method of aligning a wheel of a medical device begins at step 400, during which medical device 10 is positioned on a ground surface. Medical device 10 includes at least one wheel 20, allowing medical device 10 to be translated along the ground surface. As such, a medical professional can move medical device 10 around an operating room.

The positioning of medical device 10 is often integral to the success of a medical procedure. For example, if medical device 10 is a fluoroscopy machine, the angle of the machine in relation to the patient is a vital component of the medical procedure. Depending on the requirements of a particular medical procedure, or the varying body characteristics between patients, medical device 10 may be moved away from its initial position. Failure to replicate the initial position after medical device 10 has been moved can cause a failure of the procedure, or medical complications. Accordingly, step 410 includes surrounding wheel 20 of medical device 10 with wheel alignment guide 100. If wheel alignment guide 100 includes only first body member 105a, step 410 includes placing first body member 105a on the ground surface such that wheel 20 is oriented along the longitudinal axis of first body member 105a, spanning from L-shaped edge 250b to L-shaped edge 250c. Alternatively, if wheel 20 is oriented along the lateral axis of first body member 105a, wheel 20 is surrounded by central longitudinal edge 260a and the lateral edges adjacent to central longitudinal edge 260a, such that wheel 20 extends away from central longitudinal edge 260a.

If wheel alignment guide 100 includes first body member 105a and second body member 105b, step 410 includes placing at least one first body member 105a and second body member 105b on the ground surface, such that wheel 20 is at least partially surrounded by one of the body members. The remaining body member is then placed adjacent to the placed body member during step 420, such that first body member 105a and second body member 105b together surround wheel 20 within opening 110. If only first body member 105a is used to surround wheel 20, step 420 may not be performed.

Regardless of whether only one body member or multiple body members are used to surround wheel 20, wheel alignment guide 100 serves as a visual indication of the desired position of medical device 10, in the event that medical device 10 is translated away from the desired position. Moreover, wheel alignment guide 100 secures to the ground surface during steps 410 and 420, making it difficult to inadvertently disconnect wheel alignment guide 100 from the ground surface. For example, if wheel alignment guide 100 is made of a static cling vinyl material, wheel alignment guide 100 forms an adhesive-like relationship with the ground surface via an electrostatic connection. Alternatively, wheel alignment guide 100 may form an electric or magnetic connection with a complementary charge on the ground surface.

The method may then proceed to step 430, during which wheel 20 is pivoted within wheel alignment guide 100. Depending on the requirements of the medical procedure, it may be desirable to orient wheel 20 in a direction parallel to handle 30, or perpendicular to handle 30. By pivoting wheel 20 to different orientations, medical device 10 may be translated in different directions. Due to the plurality of concave interior edges 240a-d discussed above, wheel alignment guide 100 facilitates the pivoting of wheel 20 between orientations.

During step 440, medical device 10 is translated away from wheel alignment guide 100. As discussed above, it may be necessary to move medical device 10 away from its desired position. For example, a surgeon may require access to a patient that is blocked by the desired position of medical device 10. Alternatively, the area around medical device 10 may require cleaning between medical procedures. In such a situation, it is desirable to move medical device 10 away from wheel alignment guide 100, with wheel alignment guide 100 remaining in the desired position. Accordingly, during step 450, wheel 20 is repositioned within wheel alignment guide 100 in the desired position of medical device 10. In step 450, a user translates medical device 10 toward wheel alignment guide 100, which remains located in its initial position throughout the medical procedure. Wheel alignment guide 100 receives wheel 20 of medical device 10, thereby repositioning wheel 20 within wheel alignment guide 100, returning medical device 10 to its initial and desired location. Wheel alignment guide 100 thereby ensures that medical device 10 is correctly repositioned, increasing the likelihood success of the medical procedure.

It is appreciated that alternative embodiments of wheel alignment guide 100 may be used as visual indicators for the placement of non-medical devices. For example, wheel alignment guide 100 may be used to efficiently store an item within an enclosed space, such as a garage, such that the item can easily be restored to a desired position. Similarly, wheel alignment guide 100 may be used with a device that does not include traditional wheels, so long as the device is movable. For example, an operating table including stationary legs may need to be placed in a particular spot within an operating room. Accordingly, wheel alignment guide 100 may be used to surround a stationary leg on the table to provide a visual indication of the current placement of the table.

In addition, it is appreciated that wheel alignment guide 100 may be made of a material that is capable of being sterilized for use within an operating room. In an embodiment, wheel alignment guide 100 is packaged in a sterile, single-use, disposable packaging prior to being used in the operating room. The material of wheel alignment guide 100 is flexible, allowing first and second body members 105a, 105b to bend and deform, such that the body members can be flexed to more easily at least partially surround wheel 20.

Figure 5:
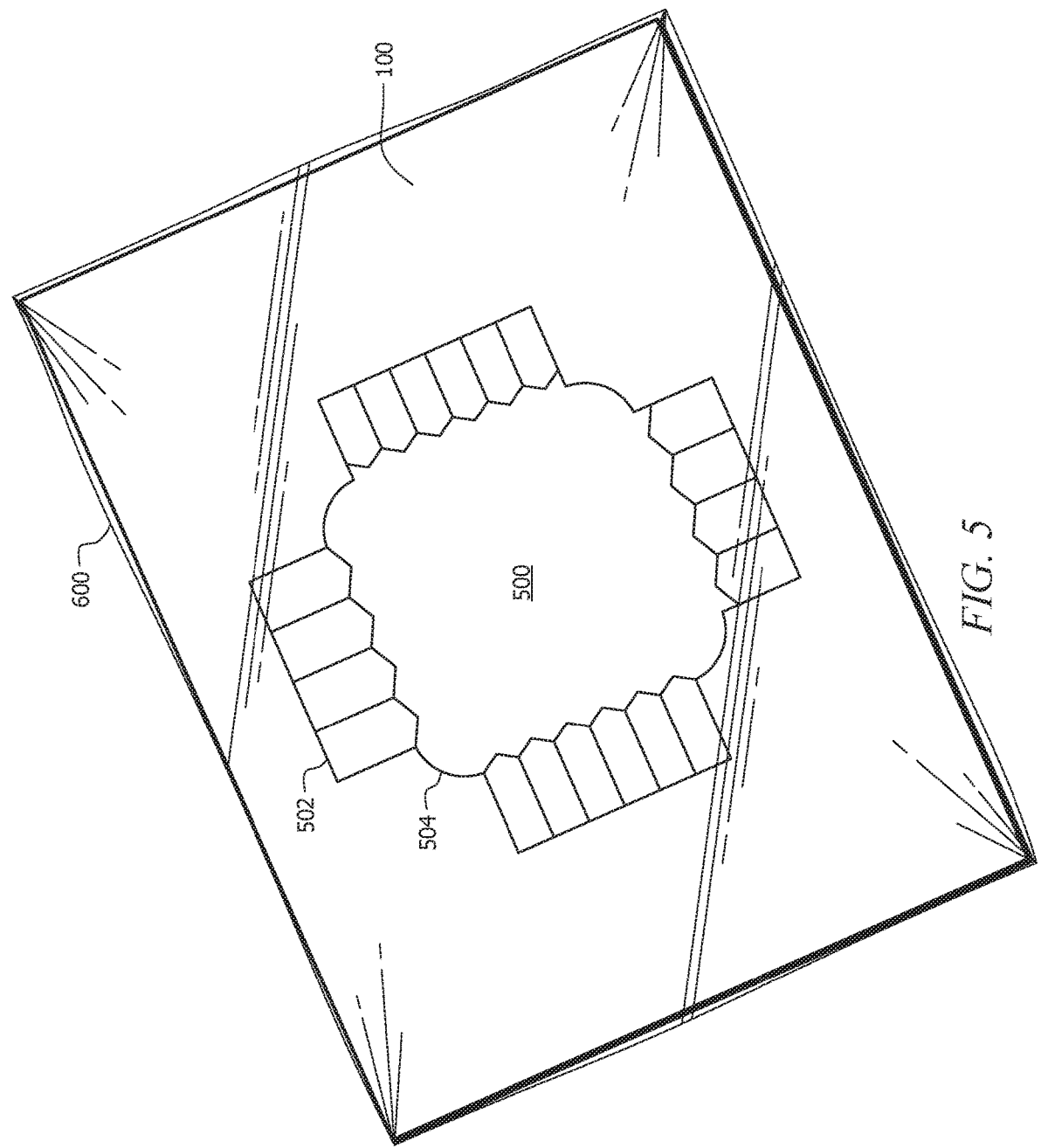
FIG. 5 is an orthogonal view of a kit including a wheel alignment guide and detachable alignment indicia, in accordance with an embodiment of the present invention.
Figure 6:
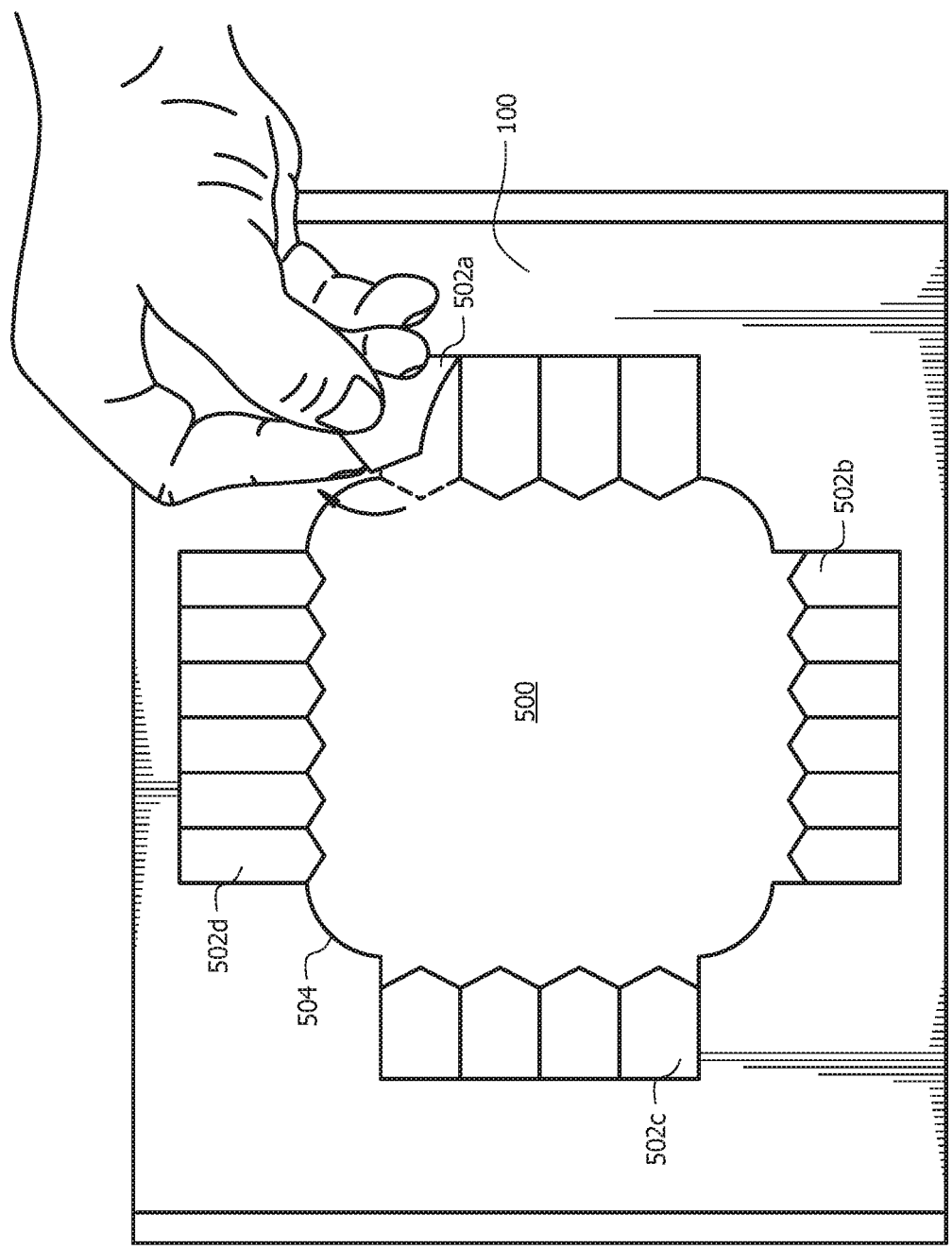
FIG. 6 is an orthogonal view of the detachable alignment indicia of FIG. 5.
Figure 7:
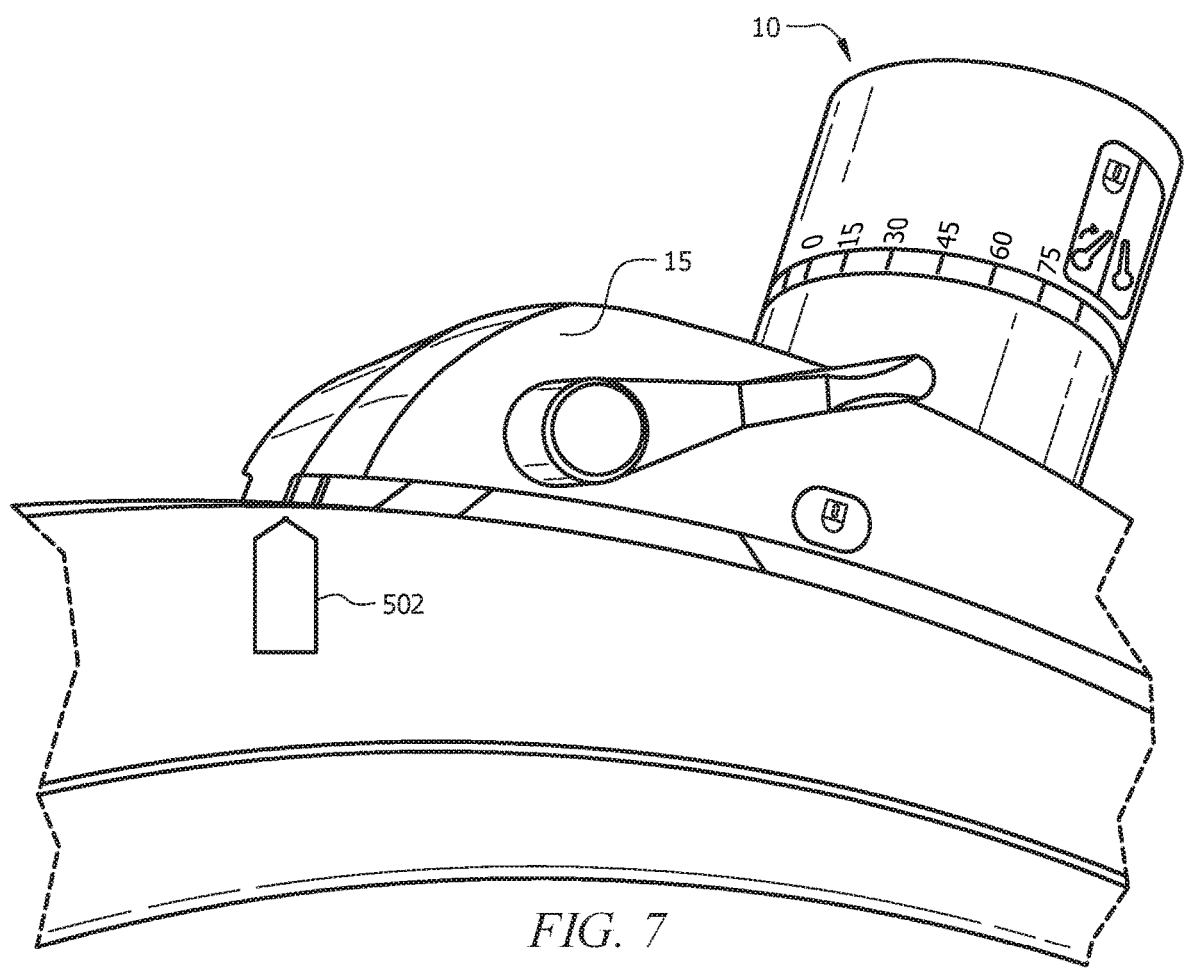
FIG. 7 is a perspective view of the detachable alignment indicia of FIG. 5 used in combination with a medical device.

FIGS. 5-7 depict secondary orientation guide 500 that may be packaged together with wheel alignment guide 100 into kit 600, as shown in particular in FIG. 5. In an embodiment, secondary orientation guide 500 is detachable from wheel alignment guide 100 within kit 600. In an alternative embodiment, secondary orientation guide 500 is separate from wheel alignment guide 100. Regardless of the attachment between secondary orientation guide 500 and wheel alignment guide 100, in an embodiment, secondary orientation guide 500 is sized and shaped to be received by opening 110 defined by wheel alignment guide 100 prior to the placement of wheel alignment guide 100 on a ground surface for use in aligning a wheel. As such, secondary orientation guide 500 includes a perimeter that is slightly smaller than a perimeter of opening 110, such that secondary orientation guide 500 can be received within opening 110 without obstruction. In addition, in an embodiment, particularly as shown in FIG. 5, secondary orientation guide 500 includes a plurality of convexly curved surfaces 504 that are sized and shaped to be reciprocal to the plurality of concave edges 240 of wheel alignment guide 100, such that secondary orientation guide 500 fits within opening 110 that is partially defined by concave edges 240. Furthermore, in an embodiment, secondary orientation guide 500 includes an associated height from a bottom surface to a top surface that is approximately equal to an associated height of wheel alignment guide 100 to provide a secure connection between the components, particularly when packaged together in kit 600. Secondary orientation guide 500 is flexible, similar to wheel alignment guide 100.

Secondary orientation guide 500 includes one or more detachable alignment indicia 502 disposed about a surface thereof. In an embodiment, secondary orientation guide 500 includes a plurality of alignment indicia 502, as shown in particular in FIGS. 5-6. Alignment indicia 502 are disposed on secondary orientation guide 500 such that indicia 502 can be easily gripped by a user and detached from secondary orientation guide 500 for external placement. For example, as shown in FIG. 7, one or more alignment indicia 502 can be placed on medical device 10 to indicate a particular orientation of medical device 10. As shown in FIG. 7, medical device 10 includes a moveable arm 15 that is oriented at a particular angle during a medical procedure. During use, arm 15 is moved out of position, and requires a repositioning to the original orientation later during the procedure. As shown in FIG. 7, alignment indicia 502 attaches to medical device 10 to indicate an orientation of arm 15, such that arm 15 can be returned to the designated orientation after being moved.

Each of the one or more alignment indicia 502 can be of a different size to be applied to devices and surfaces of various dimensions. For example, as shown in FIGS. 5-6, the plurality of alignment indicia 502 can vary in lengths and widths depending on the requirements of the surfaces to which the indicia are applied. Specifically, FIG. 6 depicts alignment indicia 502a that are wide and long; alignment indicia 502b that are narrow and short; alignment indicia 502c that are wide and short; and alignment indicia 502d that are narrow and long. The widths of alignment indicia 502a, 502c are depicted as equal to one another, as are the widths of alignment indicia 502b 502d. Similarly, the lengths of alignment indicia 502a, 502d are depicted as equal to one another, as are the lengths of alignment indicia 502b, 502c. In alternative embodiments, each of the one or more alignment indicia 502 can be of equal size, including equal surface area and volume, with equal length and width dimensions.

The bottom surface of each alignment indicia 502 is attachable to ground surfaces and surfaces of devices, such as medical devices, similar to bottom side 210 of wheel alignment guide 100. Accordingly, as discussed above in relation to bottom side 210 of wheel alignment guide 100, in an embodiment, each alignment indicia 502 includes a charge that is adapted to form a connection with a complementary charge of either a ground surface, a device, a wall, or other surface to which alignment indicia 502 is placed. The charge may be a magnetic charge, an electric charge, a static cling charge, or other similar charge that allows for a complementary relationship between alignment indicia 502 and the surface. For example, the static cling vinyl material allows each alignment indicia 502 to adhere to a surface via electrostatic forces, rather than adhesives. As such, alignment indicia 502 provides a sterile surface that is used to mark and indicate a selected orientation of a device in the event that the device is moved to another orientation. In an embodiment, the entire bottom surface area of secondary orientation guide 500 is made of a similar material as wheel alignment guide 100, such that secondary orientation guide 500 is similarly charged as wheel alignment guide 100. However, it is appreciated that the bottom surface of each alignment indicia 502 may alternatively include an adhesive that does not leave a residue, such that alignment indicia 502 can be secured to a surface due to the adhesion forces between the indicia and the surface.

Glossary of Claim Terms

Charge: is a physical property of a material that causes the material to experience a force when disposed proximate to a complementary charge. For example, a charge may be an electrostatic charge, electric charge, or magnetic charge.

Flexible: as used herein, "flexible" means capable of bending or folding without breaking.

Ground surface: is a surface upon which human beings can stand and equipment can rest. For example, a ground surface may be a floor of an operating room.

Medical device: is an apparatus or machine used in furtherance or aid of a medical procedure. For example, a medical device may be a fluoroscopy machine used to scan a patient during surgery.

Static cling vinyl: is a vinyl material capable of coupling to a surface via an electrostatic charge.

Taper: as used herein, "taper" means to gradually become smaller toward an end.

Wheel: is a substantially rounded structure capable of lateral translation along a ground surface. The wheel may be a swivel caster, rigid caster, alloy wheel, bicycle wheel, omni wheel, or the like, and may be made of plastic, rubber, cast iron, aluminum, stainless steel, polyurethane, or any other material capable of lateral translation.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A wheel alignment guide comprising:
   a body member having a top side opposite a bottom side, the bottom side configured to rest on a ground surface, the body member including a distal end opposite a proximal end;
   a pair of opposing concave edges disposed at the proximal end, each concave edge extending toward the distal end,
   wherein a portion of a perimeter of the body member defined by the proximal end is sized and shaped to receive a wheel of medical device, and
   wherein each concave edge is adapted to allow the wheel to pivot between lateral and longitudinal orientations with respect to the body member.

2. The wheel alignment guide of claim 1, wherein:
   the body member is of a flexible static cling vinyl material that is adapted to securely couple to the ground surface via an electrostatic connection.

3. The wheel alignment guide of claim 1, wherein the body member is a first body member, further comprising:
   a second body member having a top side opposite a bottom side, the bottom side configured to rest on a ground surface, the second body member including a distal end opposite a proximal end with a pair of opposing concave edges disposed at the proximal end, each concave edge extending toward the distal end,
   wherein the proximal end of the second body member is disposed adjacent to the proximal end of the first body member with a gap therebetween.

4. The wheel alignment guide of claim 3, wherein:
   the portion of the perimeter of the first body member defined by the proximal end and a portion of a perimeter of the second body member defined by the proximal end together define an opening that is configured to receive the wheel of the medical device.

5. The wheel alignment guide of claim 4, wherein:
   the opening is cross-shaped, including a first portion perpendicular to a second portion, the first and second portions intersecting at their respective midpoints, the first and second portions connected through the pair of concave edges of the first body member and the pair of concave edges of the second body member.

6. The wheel alignment guide of claim 4, further comprising:
   a secondary orientation guide including a perimeter that is sized and shaped to be removably received within the opening, the secondary orientation guide including at least one detachable alignment indicia configured to indicate an orientation of the medical device.

7. The wheel alignment guide of claim 6, wherein:
   the at least one detachable alignment indicia includes a bottom surface of a flexible static cling vinyl material that is adapted to securely couple to a surface of the medical device via an electrostatic connection.

8. The wheel alignment guide of claim 1, wherein:
   the distal end of the body member tapers from the bottom side of the body member to the top side of the body member, such that the bottom side has a greater surface area than the top side.

9. A wheel alignment guide comprising:
   a body member having a top side opposite a bottom side, the bottom side configured to rest on a ground surface, the body member having a perimeter defined by:
   a distal longitudinal edge spanning along a longitudinal axis of the body member;
   a pair of opposing lateral edges extending perpendicularly away from opposing ends of the distal longitudinal edge, each lateral edge spanning along a lateral axis of the body member;
   a pair of proximal longitudinal edges, each proximal longitudinal edge extending perpendicularly away from one of the pair of lateral edges toward a central axis of the body member;
   a pair of L-shaped edges coupled to each of the pair of proximal longitudinal edges, each L-shaped edge extending toward the central axis of the body member; and
   a pair of concave edges coupled to each of the pair of L-shaped edges, each concave edge extending toward the central axis of the body member,
   wherein the perimeter of the body member defines an opening that is configured to receive a wheel of a medical device, and
   wherein the pair of concave edges are adapted to allow the wheel of the medical device to pivot between lateral and longitudinal orientations with respect to the lateral and longitudinal axes of the body member.

10. The wheel alignment guide of claim 9, wherein:
    the body member is of a flexible static cling vinyl material that is adapted to securely couple to the ground surface via an electrostatic connection.

11. The wheel alignment guide of claim 9, wherein the body member is a first body member, further comprising:
    a second body member spaced apart from the first body member with a gap therebetween, the second body member having a top side opposite a bottom side, the bottom side configured to rest on a ground surface, the second body member having a perimeter defined by:
    a distal longitudinal edge spanning along a longitudinal axis of the second body member;
    a pair of opposing lateral edges extending perpendicularly away from opposing ends of the distal longitudinal edge, each lateral edge spanning along a lateral axis of the second body member;

a pair of proximal longitudinal edges, each proximal longitudinal edge extending perpendicularly away from one of the pair of lateral edges toward a central axis of the second body member;

a pair of L-shaped edges coupled to each of the pair of proximal longitudinal edges, each L-shaped edge extending toward the central axis of the second body member; and a pair of concave edges coupled to each of the pair of L-shaped edges, each concave edge extending toward the central axis of the second body member.

12. The wheel alignment guide of claim 11, wherein:

the perimeter of the first body member and a perimeter of the second body member together define the opening that is configured to receive the wheel of the medical device.

13. The wheel alignment guide of claim 12, wherein:

the opening is cross-shaped, including a first portion perpendicular to a second portion, the first and second portions intersecting at their respective midpoints, the first and second portions connected through the pair of concave edges of the first body member and the pair of concave edges of the second body member.

14. The wheel alignment guide of claim 12, further comprising:

a secondary orientation guide including a perimeter that is sized and shaped to be removably received within the opening, the secondary orientation guide including at least one detachable alignment indicia configured to indicate an orientation of the medical device.

15. The wheel alignment guide of claim 9, wherein:

the distal longitudinal edge tapers from the bottom side of the body member to the top side of the body member, such that the bottom side has a greater surface area than the top side.

16. The wheel alignment guide of claim 9, wherein:

the bottom side of the body member has a charge, the bottom side being adapted to form a connection with a complementary charge of the ground surface.

17. The wheel alignment guide of claim 16, wherein:

the charge is a magnetic charge, and the bottom side is adapted to magnetically couple with a corresponding magnet on the ground surface.

18. The wheel alignment guide of claim 16, wherein:

the charge is an electric charge, and the bottom side is adapted to electrically couple with the ground surface.

19. A wheel alignment guide comprising:

a first body member having a top side opposite a bottom side, the bottom side configured to rest on a ground surface, the first body member including a distal end opposite a proximal end, with a pair of opposing concave edges disposed at the proximal end, each concave edge extending toward the distal end;

a second body member spaced apart from the first body member by a gap, the second body member having a top side opposite a bottom side, the bottom side configured to rest on a ground surface, the second body member including a distal end opposite a proximal end, with a pair of opposing concave edges disposed at the proximal end, each concave edge extending toward the distal end;

a cross-shaped opening defined by the proximal ends of the first body member and the second body member, the opening being configured to receive a wheel of a medical device therein, wherein each concave edge is adapted to allow the wheel to pivot between lateral and longitudinal orientations with respect to the first and second body members.

20. The wheel alignment guide of claim 19, further comprising:

a secondary orientation guide including a perimeter that is sized and shaped to be removably received within the opening, the secondary orientation guide including at least one detachable alignment indicia configured to indicate an orientation of the medical device.

* * * * *